United States Patent
Potts et al.

(10) Patent No.: US 7,150,991 B2
(45) Date of Patent: Dec. 19, 2006

(54) METHOD TO PRESERVE CELLS

(75) Inventors: Malcolm Potts, Blacksburg, VA (US); Richard Helm, New Castle, VA (US); Mark S. Berninger, N. Potomac, MD (US); Herbert A. Avila, Monrovia, MD (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 396 days.

(21) Appl. No.: 10/402,925

(22) Filed: Apr. 1, 2003

(65) Prior Publication Data

US 2004/0023202 A1 Feb. 5, 2004

(51) Int. Cl.
*C12N 5/00* (2006.01)

(52) U.S. Cl. .................................................. 435/374

(58) Field of Classification Search .................. None
See application file for complete search history.

(56) References Cited

U.S. PATENT DOCUMENTS 6,528,309 B1 * 3/2003 Levine ....................... 435/374

OTHER PUBLICATIONS

You et al., "Cellular Characteristics of primary and immortal canine embryonic fibroblast cells", Experimental & Molecular Medicine 36 (4) : 325-335 (2004).*

Christman et al., "Modulation of p53 expression and its role in the conversion to a fully immortalized chicken embryo fibroblast line", FEBS Letters, 579 (30) : 6705-15 (2005).*

Drissi et al., "c-Myc-mediated regulation of telomerase activity is disabled in immortalized cells", J, Biol. Chem. 276 (32) : 29994-30001 (2001).*

Kyo et al., "Successful immortalization of endometrial glancular cells with normal structural and functional characteristices", American J. Pathology 163 (6) : 2259-69 (2003).*

Handschack et al., A simple method for cloning and replica plating of mammalian cells using multi.-cellular spheroids, Acta Biologica et Medica Germanica 36 (10) : 1429-1434 (1977).*

Wigle et al., Increased Thermoresistance Developed During Growth of Small Multicellular Spheroids, J. Cellular Physiology 122 : 281-89 (1985).*

Dugan et al., "Phenotypic Diversification of a Cultured Tumor Line as a Function of Substratum", J. Supramolecular Structure and Cellular Biochemistry 15 (4) : 317-326 (1981).*

* cited by examiner

*Primary Examiner*—Sandra E. Saucier
(74) *Attorney, Agent, or Firm*—Whitham, Curtis, Christofferson & Cook, PC

(57) ABSTRACT

Methods are disclosed that provide for the preservation of living human and other cells at room temperature or higher temperatures which can be applied to research, medical and defense applications. These methods represent a significant improvement relative to currently used methods that employ preservation at cryogenic temperatures. Using these methods, living human and other cells can be stored at room temperature or higher, and subsequently be recovered as living cells capable of dividing and exhibiting other well recognized properties of living cells.

9 Claims, No Drawings

METHOD TO PRESERVE CELLS

This invention was made using funds from grants from the Department of Defense-Naval Research Laboratory (N00014-01-1-0852) and N00173-02-1-G-016. The government may have certain rights in this invention.

BACKGROUND OF THE INVENTION

The present invention generally relates to field of the stabilization and preservation of cells. More particularly, the present invention relates to stabilization and preservation of cells at room temperature or higher. The invention provides a method for the preparation of cells that have been induced to aggregate to form spheroid or spheroid-like cell aggregations and the partial desiccation of these aggregates, their storage at room temperature or above and their rehydration, all of the preceding steps carried out so as to maintain the integrity and viability of the cells, including their ability to divide and give rise to a growing population of cells. The invention further provides for a method for the preservation of whereby cells are deposited upon an agarose surface and desiccated so as to prevent the aggregation of the cells to form spheroids or spheroid-like aggregates, the storage of such cells following desiccation at room temperature, and their rehydration; all of the preceding steps carried out so as to maintain the integrity and viability of the cells, including their ability to divide and give rise to a growing population of cells.

DESCRIPTION OF THE RELATED ART

Cells grown in culture have a multitude of uses in biomedical research, diagnostic medicine, and production of high value biologicals for human therapy. Considerable research is being funded by pharmaceutical and biotechnology companies and government funding agencies such as the United States National Institutes of Health to develop cell-based treatments for a number of widespread and serious diseases including Parkinson's disease, diabetes, and cancer. It is generally understood among cell biologists that such cells must be maintained as growing cultures or stored at cryogenic temperatures. Both alternatives entail costs and inconvenience and limit uses outside a laboratory environment. A method to preserve cells at room temperature would have considerable value to the research and medical communities and make possible application of such cells outside the laboratory context. One example of such a non-laboratory application is the use of living cells in remote deployable sensors for the detection of biological or chemical warfare or terrorism agents. Genetically engineered cells have been developed that respond to infectious or toxic agents by producing a distinctive output. Use of such sensors by homeland defense or military personnel require that the biological component of the sensor be stable at ambient temperatures. Other potential uses include provision of viable cells to clinical laboratories for diagnosis of viral infections, and for therapy, especially in emergency situations remote from cryogenic storage facilities, including field hospitals near a battlefield.

A number of organisms in Nature have the capacity to survive prolonged periods in a desiccated state and be restored to viability upon rehydration. These organisms are referred to as anhydrobiotic organisms and the processes by which they achieve this viable desiccated state are referred to as anhydrobiosis. These organisms use a variety of mechanisms to achieve this environmental adaptation. Cells and even entire organisms (e.g. bears) can enter a state of reduced metabolic activity during which they utilize far less nutrients and produce less waste products than when growing or full active. An example of such a resting state is seen when cells exhibit contact inhibition after growing to form a monolayer of cells attached to a surface, the plastic used in commercially available flasks and plates sold for cell culture being an example of such a surface.

Cells derived from mammals and other higher eukaryotes, including man, can be grown or cultured outside the body. Such cells are generally referred to as tissue culture cells. When cultured according to methods well known in the art these cells can grow and divide. Such cells grown in culture may also maintain a resting state in which they do not divide but remain viable and capable of resuming cell division and growth if later transferred to an environment conducive to cell division and growth.

Recently, two methods have been described by which mammalian cells have been desiccated, stored at room temperature, and then rehydrated; PCT/US 00/16603, and Guo N. et. al. (2000). However, alternative methods that use less costly reagents and provide longer storage at room temperature are desired.

Most cell lines used in biomedical research are grown in plastic tissue culture flasks or plates with the cells attached to the bottom plastic surface of the flask or plate. When grown in this conventional manner, most cells assume a spread out and somewhat flat morphology and maintain close attachment to the surface of the flask or plate. It is possible to induce a wide variety of cell types to assume an alternative morphology in which the cells round up, become detached from the surface of the plate and aggregate into essentially spherical balls containing hundreds to thousands of cells. Such balls of cells are termed spheroids and have been the object of biological research. As used herein the term "spheroids" includes aggregates of cells produced by the methods herein described as well as spheroids described in the scientific literature that may be produced using other methods. Spheroids can be induced to form by depositing cells upon a bed of agarose submerged under a layer of fluid growth media.

SUMMARY OF THE INVENTION

A method is herein described by which mammalian tissue culture cells are grown so as to induce the aggregation of cells into spheroids, such as by plating the cells on a substratum of agarose, but is not limited to this method for inducing aggregation, and absent any recognized agents that mediate desiccation tolerance (e.g. trehalose or the glycan produced by the anhydrobiotic cyanobacterium *Nostoc commune*). The spheroids are then partially desiccated at room temperature, are stored at room temperature, and are subsequently restored to viability by rehydrating the dried spheroids by addition of liquid growth media.

Another method is described in which cells are deposited on an agarose surface in a substantially minimal volume of media and soon thereafter are placed in a low humidity environment to remove excess fluid water by evaporation. In this method excess water is removed sufficiently quickly that the cells deposited on the agarose do not aggregate to form spheroids or spheroid-like structures.

"Desiccation" is defined for the purpose of this invention as the removal, by evaporation or other means, of fluid water surrounding the cells and is not intended to imply or require the removal of all water or any particular amount of water. "Fluid water" or "Fluid media" is defined for the purpose of this invention as water or media that is not contained within a gel or a cell and can flow freely. It is assumed that considerable water remains within the cells through all steps of this invention. "Cells" for the purpose of this invention refer to eukaryotic cells derived from multicellular organisms that can grow as individual cells in culture.

The above referenced methods for preservation of cells at room temperature utilize reagents known to be associated with desiccation tolerance in nature e.g. trehalose or a glycan produced by the anhydrobiotic cyanobacterium *Nostoc commune*. Agarose, however, is a refined product of agar, which is produced by a marine organism and is not known to be associated with anhydrobiosis in Nature. In the present invention addition of agents associated with desiccation tolerance in Nature are not necessary. It is, however, recognized that in some instances their addition could enhance stability of the desiccated material described herein.

DESCRIPTION OF ILLUSTRATIVE EMBODIMENTS OF THE INVENTION

The methods disclosed herein overcome limitations in the prior art and improve techniques for cell preservation, particularly for the preservation of cells outside the laboratory environment where cryogenic storage is impractical. In respect to all the embodiments described herein below cells are grown in culture and manipulated so as to maintain sterility using standard techniques well known to those skilled in the art of cell culture.

Human embryonic kidney cells line 293H (Invitrogen Corporation, Carlsbad Calif.), a derivative of 293 cells, a widely used cell line in biomedical research, or CHO K1 cells, a cell line derived from Chinese hamster (available from the American Type Culture Collection—ATCC) or P-19 cells a cell line derived from mice (available from the ATCC), or human B cell line Yp 24-6 a genetically engineered line for the detection of *Yersinia pestis* (Lincoln Laboratory of the Massachusetts Institute of Technology), or human fibroblasts (ATCC CCL-116) are thawed from cryogenically stored stocks and grown in culture in plastic tissue culture flasks as a monolayer using routine procedures until a continuously growing stable culture is developed. Cells are grown in liquid 1×GIBCO Dulbecco's Modified Eagle Medium (high glucose; D-MEM; Invitrogen) or RPMI 1640 (Invitrogen) or alpha MEM (Invitrogen) or other suitable media containing a final concentration of 10% w/v fetal bovine serum (Invitrogen) and 1×MEM with non-essential amino acids (Invitrogen), at 37° C., in an atmosphere of 5% v/v carbon dioxide and high humidity, in the dark. Cultures are maintained as monolayers in Nunclon tissue culture flasks (Nunc, Denmark, catalog #156367).

Preparation of Agarose Coated Plates

Agarose coated plates are prepared according to the steps listed below:

1. Add 0.375 grams Sigma agarose Type 1-A low EEO (cat. A-0169) (lot # 90K1343; EC No. 232-731-8) to 25 milliters Distilled water (1.5% w/v) or add 0.3 grams Sigma agarose Type 1-A EEO and 0.075 grams of AgarMate (Diversified Biotech) to 25 milliliters of distilled water.
2. Autoclave the resulting mixture.
3. Add 50 ml of pre-warmed DMEM or RPMI 1640 or alpha MEM as appropriate to the cells to be preserved, to the mixture and pour immediately. (A failure to pour the plates immediately will result in rapid hardening of the agarose). Final concentration is 0.5% w/v agarose.
4. The agarose is poured to give a depth of 4 to 5 millimeter Fifty milliliter of agarose provides enough material to coat approximately 10 plates
5. Typically Fisher brand 100×15 millimeter standard sterile polystyrene plates are used (Fisher Scientific Pittsburg Pa. cat. 08-757-13).
6. Allow plates to gel and supplement them with 10 milliliter of DMEM (overlay).
7. Plates may be stored refrigerated before or after addition of 10 milliliter of DMEM.

Preparation of Agarose Coated Tube Caps

The caps of plastics vials sold for storage of biochemical substances (catalog number 65.715.023; Sarstedt Aktiengesellshaft and Company, Germany) are used to hold an agarose bed upon which cells are deposited according to the present invention. Other similarly shaped containers, including standard Petri dishes or multiple well plasticware commonly sold for growth of tissue culture cells, are also suitable. If containers of greater of smaller size are used the volume of agarose is adjusted to maintain a depth of the agarose bed of approximately 1 millimeter. Agarose at a concentration of 0.5% (w/v) containing cell growth media is prepared as per steps one through three of "Preparation of agarose coated plates" above. 100 microliters of the above agarose solution is pipetted while molten into the center of each cap (catalog number 65.715.023; Sarstedt Aktiengesellshaft and Company, Germany) and the agarose is allowed to gel. Agarose coated caps are best used immediately to preserve cells, but may be stored under high humidity at 4 degrees Celsius.

Preparation of Spheroids

Adherent cells from a liquid culture are obtained following treatment with trypsin-EDTA (Invitrogen Corporation); 0.05% trypsin, 0.53 mM EDTA (Invitrogen Corporation). Typically, the medium of a 10-milliliter culture in a Nunc tissue culture flask is poured off and the cells are rinsed once with phosphate buffered saline. The cells are then incubated with 3 ml trypsin-EDTA at room temperature for approximately 40 seconds. Six milliliters of fresh medium is then added to the cells that are thoroughly dispersed using a pipette. 0.5 milliliter of the suspension is used to inoculate a standard 100×15 millimeter plate having a substratum of agarose (prepared as described above) and the plate is then returned to the high humidity, 5% v/v $CO_2$, 37° C. incubator. The typical morphology and growth habit of 293H cells, CHO K1 cells and P-19 cells changes when plated on a substratum of agarose. Cells initially loose their characteristic projections, become spherical and become unattached or only very loosely attached to the agarose substratum. These small spherical cells then aggregate to form large spherical aggregates, spheroids. After a growth period of 1 to 2 weeks, most of the 293H cells, CHO K1 cells or P-19 cells have aggregated to form spheroids.

Preparation and Storage of Cells on Agarose Coated Caps

In the following method the tops or caps of small plastic vials are used as small cell culture dishes and the tubes are used as tops or caps. Each cap is filled with approximately 100 microliters molten 0.5% agarose containing growth media supplemented with serum or other materials as described above. The agarose is permitted to gel at room temperature there providing an agarose-coated cap. Cells that have been recently removed from standard tissue culture flasks by trypsinization are suspended to a concentration of $5×10^6$ to $2.5×10^7$ per milliliter in media supplemented with fetal bovine serum and 2 millimolar glutamine or GlutaMax (Invitrogen Corporation). Twenty to fifty microliters of the above cell suspension is added to each agarose-coated cap thereby making a cell-agarose assembly. The cells and the cap are immediately placed in a desiccation chamber and incubated at low humidity (approximately 20% relative humidity) at room temperature for 2 to 3 hours. Following this incubation the tubes are screwed into the caps to seal the caps and tubes to form sealed cap/tube assemblies. The sealed tube/cap assemblies containing cells above the agarose used to coat the cap are stored at room temperature.

Design of a Drying Chamber

This system has been developed at the Center for Genomics at the Virginia Polytechnic Institute and State University in Blacksburg Va. where it is known as the Controlled Atmosphere Culture Desiccation System (CHSDS). The CHCDS consists of a core modular component consisting of two closed atmosphere compartments each having dimensions of approximately (width to length to height) for an overall dimensions of the bi-chamber CHCDS of approximately 24 inches by 25 inches by 24 inches (width to length to height). This chamber is available from Terra Universal Inc. North Harbor Blvd. Anaheim, Calif. 92805. Each chamber is fitted with a data interface port such as an RS 232 port to allow electronic connection with instruments located inside the chamber. Each chamber is also retrofitted with intake and outtake ports of approximately 1 inch diameter each to channel flow of air or nitrogen into and out from each chamber. Each chamber is provided with a Nitroplex Nitrogen humidity controller (available from Terra Universal Inc.) and retrofitted with a Micromega 77000 Series Temperature Controller and an Omega "T" Type in-line air process heater (both available from Omega Engineering Inc. One Omega Drive Stamford, Conn. 06907).

Operation of a Drying Chamber

A chamber capable of holding multiple standard tissue culture plates and permitting control of the flow of input air and/or nitrogen, means to control the humidity of input air and/or nitrogen, and means to control the temperature of the chamber and its contents is used to dry cells. The humidity of the atmosphere in the chamber can be adjusted by adjusting the mixture of air and nitrogen pumped into the chamber. Nitrogen as delivered in a compressed tank having very low humidity is mixed with room air that can vary in humidity according to the local weather conditions. Additional control of relative humidity in the chamber can be achieved by placing open vessels therein that contain solutions of different water potential e.g. different concentrations of glycerol; saturated salt solutions etc.) By regulating the mixing of the two gases a relative humidity of approximately 20% can be maintained. An example of such a drying chamber is detailed above. Such a chamber has been established to be suitable for drying cells according to this invention, but other chambers of larger, smaller or different design which provide essentially the same environment to the cells during drying as provided by this chamber will also be suitable. Different levels of relative humidity may also be found to be better suited to different cell types.

Desiccation of Spheroids

After the cells have adopted the spheroid morphology the medium overlaying the basal agarose layer is removed carefully using a pipette taking care to minimize the inadvertent removal of spheroids. The pipette is held vertically for several seconds so that any spheroids accidentally removed collect at the tip (through gravity) and can be returned to the plate with minimal addition of liquid. Following removal of the excess media the plate is placed in a desiccation chamber such as described above and desiccated for 12 to 18 hours. During drying the temperature in the chamber is held to approximately 20 degrees Celsius, the relative humidity is held to approximately 20%, and the flow of air or nitrogen is held to approximately 5 cubic feet per minute, providing for complete replacement of the chamber volume every approximately 40 seconds. During the desiccation procedure the chamber is kept in darkness. At the initial stages of the desiccation process air is present in the chamber. Automatically controlled pulses of dry nitrogen gas serve to maintain the relative humidity at 20% during the approximately 12 to 18 hours of the drying process.

Storage of Desiccated Spheroids—Method 1

Agarose plates supporting the spheroids (from which media has been removed) are stored for 5 days at 37 degrees Celsius in a standard tissue culture incubator in high humidity atmosphere of 5% $CO_2$ and 95% air. During storage in the tissue culture incubator the cells are in essentially total darkness except for brief periods when the door is opened to remove plates from the incubator, following which the cells are placed in Dri-Shield 2000 Moisture Barrier Bag (Static Control Components Inc., Sanford, N.C.). The bag is sealed using a Flaem Nuova model Magic Vac Champion (made in Italy). The corner of the bag is then cut to allow insertion of a tube connected to a tank of compressed nitrogen that is used to replace the air in the bag with nitrogen by blowing nitrogen into the bag for approximately one minute before sealing the bag. The sealed antistatic bag (which has a pillow-like appearance) is placed inside a Magic Vac plastic bag that is then completely evacuated and sealed. This arrangement facilitates dark storage in an essentially oxygen-free environment. Note, that while the outer bag has been evacuated the inner bag contains nitrogen and, since the bag-within-a bag assembly is held in an environment at atmospheric pressure, the pressure inside the inner bag, the pressure experienced by the cells, is the same as the air pressure inside the room in which the cells are stored.

Storage of Desiccated Spheroids—Method 2

Following removal from the drying chamber, plates containing desiccated cells are placed in a standard tissue culture incubator at 37 degrees Celsius in high humidity atmosphere of 5% $CO_2$ and 95% air. During storage in the tissue culture incubator the cells are in essentially total darkness except for brief periods when the door is opened to remove plates. The cells are then placed in Dri-Shield 2000 Moisture Barrier Bag (Static Control Components Inc., Sanford, N.C.). The bag is sealed using a Flaem Nuova model Magic Vac Champion (made in Italy). The corner of the bag is then cut to allow insertion of a tube connected to a tank of compressed nitrogen that was used to replace the air in the bag with nitrogen by blowing nitrogen into the bag for approximately one minute before sealing the bag. The sealed antistatic bag (which has a pillow-like appearance) is placed inside a Magic Vac plastic bag that is then completely evacuated and sealed. This arrangement facilitates dark storage in an essentially oxygen-free environment.

Storage of Desiccated Spheroids—Method 3

Cells are transferred to a 37 degree Celsius tissue culture incubator as described in "Storage of desiccated spheroids Method 1" above, except that instead of storing the cells in the tissue culture incubator for 5 days they are stored for 18 hours before they are transferred to bags, the air in the bags replaced with nitrogen, and sealed as described in "Storage of desiccated spheroids Method 1" above.

Rehydration of Desiccated Spheroids

The bags are surface sterilized and opened in a tissue culture hood and the plates removed. The cells are rehydrated by the addition of an overlay of DMEM medium that contains twice the normal concentration (20% v/v) of the same fetal bovine serum used to grow the cells as described above. These operations are performed in a lamina flow hood using standard sterile technique. The cell suspension is removed and transferred to a new sterile Nunclon tissue culture flask under standard growth conditions for liquid tissue culture.

EXAMPLE 1

A culture of hamster cells line CHO KI was established in standard tissue culture flasks. Cells from this culture were transferred to Petri plates coated with agarose and incubated for 10 days until the cells formed spheroids or spheroid like aggregates of cells. Media was carefully removed and the cells were desiccated as described in "Desiccation of spheroids" above in the drying chamber described above. After storage in a tissue culture incubator at 37 degrees Celsius in a humid atmosphere of 5% CO2 and 95% air (Storage of desiccated spheroids Method 2) for 11 days the cells were rehydrated with the addition of standard tissue culture media and incubated in a standard tissue culture Petri dish (not an agarose coated plate). After several days the cells were observed to have assumed a non-spheroid morphology and were dividing as single cells attached to the Petri dish surface. The cells were observed to assume their normal morphology, spread, attached, and growing as a monolayer with 2 to 3 days following rehydration.

EXAMPLE 2

Cells from a culture of Human Embryonic Kidney Cells line 293H (293H cells) growing as a monolayer in a standard culture flask were transferred to agarose coated plates prepared as described above and incubated to induce the formation of spheroids or spheroid-like aggregates. Following formation of spheroids the cells were dried as described above and stored according to "Storage of desiccated spheroids Method 1" described above. After storage for 19 days (5 days within a tissue culture incubator at 37 degrees Celsius and 12 days within a light tight bag) the cells were rehydrated using the procedure for rehydration described above and cultured in a standard Petri dish. Within 24 to 48 hours the cells are observed microscopically and a substantial percentage were observed to have a morphology characteristic of healthy growing 293H cells, that is, they were attached to the plastic surface and growing as a monolayer. After further growth these rehydrated cells were subcultured in a routine manner and an increase of cell number was observed in the subcultured Petri dish demonstrating that the rehydrated cells were restored to full viability as evidenced by their ability to divide and re-establish a growing culture. The cells were observed to assume their normal morphology, spread, attached, and growing as a monolayer within 2 to 3 days following rehydration.

EXAMPLE 3

Cells from a culture the mouse cell line P-19 (P-19 cells) growing as a monolayer in a standard culture flask were transferred to agarose-coated plates prepared as described above and incubated to induce the formation of spheroids or spheroid-like aggregates. Following formation of spheroids the cells were dried as described above and stored according to "Storage of desiccated spheroids Method 3" described above. Following storage for 7 days (18 hours within a tissue culture incubator and the remaining approximately 6 days within a sealed light tight bag at room temperature) the cells were rehydrated using the method described above and incubated, and subcultured. The cells were observed to assume their normal morphology, spread, attached, and growing as a monolayer with 2 to 3 days following rehydration.

EXAMPLE 4

Twenty-five milliliters of a 0.5% (w/v) solution of agarose DMEM medium containing 10% fetal bovine serum was added to a 185 sq, cm. NUNCLON flask and was allowed to gel. One and a half milliliters of human 293 kidney cells that had grown to 80–90% confluence (approximately concentration; $1.44 \times 10^6$ cells per milliliter were seeded onto the surface of the aforementioned 0.5% agarose together with 23.5 milliliters of DMEM. The cells were then incubated at 37 degrees Celsius in 5% $CO_2$. Incubation continued for 7 days. After 7 days the cells had aggregated to form spheroids. The media and many of the spheroids were drawn into a pipette. The spheroids were allowed to settle in the pipette and the settled spheroids were returned to the agarose-coated flask in a minimal volume of media. Excess media atop the agarose coating was wicked from the surface of the agarose using sterile Whatman paper filter. The flask was sealed with Parafilm, and then sparged in a heat sealable gas impermeable plastic bag with pure nitrogen, before sealing. The spheroids sealed in the aforementioned bags were stored at 25° C., in the dark. Three weeks following sealing of the aforementioned flasks in plastic bags 25 milliliters of DMEM (supplemented with 20% fetal bovine serum) was added to the flask and the flask was incubated at 37°/5% $CO_2$ for 3 days. Following this three day incubation 1 milliliter of media containing cells was removed and transferred to 9 milliliters of DMEM (supplemented with 20% fetal calf serum) and placed in a tissue culture flask having a surface area of 25 square cm. Note, this flask was not coated with agarose. The transferred cells attached to the plastic surface of the plate and exhibited the morphology (as observed by phase contrast microscopy) of healthy growing human 293 cells.

EXAMPLE 5

Twenty five milliliters of a 0.5% (w/v) solution of agarose MEM medium supplemented with 10% fetal bovine serum and 1% lactalbumin hydrolyzate was added to a 185 sq, cm. NUNCLON flask and was allowed to gel. Two milliliters of human fibroblasts (ATCC number CCL-116) that had grown to approximately 50% confluence (approximate concentration; $1.7 \times 10^5$ cells per milliliter) were seeded onto the surface of the aforementioned 0.5% agarose together with 23 milliliters of media. The flasks were incubated at 37 degrees Celsius in a 5% $CO_2$ atmosphere for 36 days. The cells that had not adhered to the agarose, only a small fraction having adhered to the agarose, were removed with the overlaying media and the cells were pelleted by low speed centrifugation. The pelleted cells were returned to the agarose-coated flask and stored in a sealed gas impermeable plastic bag and stored at room temperature in the dark. Following three weeks of storage cells were removed from the flask, rehydrated with 25 milliliters of media and incubated for 3 days before being transferred to a tissue culture flask (not coated with agarose). The cells attached to the plastic and had a normal healthy morphology when observed by phase contrast microscopy.

EXAMPLE 6

Human embryonic kidney cells HEK 293H (Invitrogen Corporation) were cultured per standard methods. Cells were harvested by standard trypsinization and resuspended at a concentration of $8\times10^6$ cells per milliliter in media containing 10% fetal bovine serum supplemented with 50 millimolar HEPES buffer at pH 7.2. Fifty microliters of this cells suspension were deposited upon the agarose surface of an agarose-coated cap. The cells upon the agarose-coated cap were desiccated for 3 hours. The caps were sealed by screwing a tube onto the cap to provide a sealed tube/cap assembly containing within it cells deposited upon the agarose. After storage at room temperature for various periods of time the sealed tube/cap assemblies were opened and 200 microliters of growth media was added to the tube. The cap was screwed onto the tube containing the above 200 microliters of growth media and the tube/cap assembly was gently agitated to resuspend the cells into the added growth media. The fluid growth media containing most of the cells was removed to a separate tube and cells were examined microscopically using phase contrast optics. In addition, cells were stained with Trypan Blue and live cells were enumerated microscopically using a hemocytometer. The percentage of viable cells recovered after various periods of storage following desiccation relative to the number of viable cells deposited on the agarose bed was measured by standard Trypan Blue staining and cell counting using a hemocytometer. The results are shown in Table 1 below.

TABLE 1

| Time of Sampling and Assay | Percentage Viable Cells |
| --- | --- |
| Before Desiccation | 100 |
| After Desiccation (AD) | 96 |
| 1 Day (AD) | 92 |
| 3 Days AD | 62 |
| 6 Days AD | 49 |
| 9 Days AD | 47 |
| 11 Days AD | 36 |
| 16 Days AD | 35 |
| 23 Days AD | 24 |
| 25 Days AD | 20 |

EXAMPLE 7

Cells of a human B cells line that have been genetically engineered to serve as the basis of a biosensor for *Yersinia pestis* were grown under standard conditions (RPMI 1640 media supplemented with 10% fetal bovine serum) as attached cells in standard tissue culture flasks. Cell were harvested by standard typsinization and resuspended to a concentration of $2\times10^7$ cells per milliliter in either RPMI 1640 media supplemented with 10% fetal bovine serum and 2 millimolar glutamine (Condition 1) or in RPMI 1640 media supplemented with 30% fetal bovine serum and 2 millimolar GlutaMax (Invitrogen Corporation, Carlsbad Calif.) (Condition 2). Twenty microliters of each of these cells suspensions was individually deposited upon the surface of an agarose-coated cap. The caps were then desiccated in the above-described drying chamber for 2 hours. Following desiccation empty tubes that match the above mentioned caps were screwed into the caps to form a sealed tube/cap assemblies containing therein the cells deposited upon the agarose bed. The sealed tube/cap assemblies were stored at room temperature (approximately 20 degrees Celsius). After storage for various numbers of days the sealed tube/cap assemblies were opened and 200 microliters of RPMI 1640 supplemented with 10% fetal bovine serum was added to each tube, the tube and its cap were screwed together and the media was gently mixed with the cells that had been deposited upon the agarose bed to resuspend the cells in the added media. The fluid growth media containing most of the cells was removed to a separate tube and cells were examined microscopically using phase contrast optics. In addition, cells were stained with Trypan Blue and live cell were enumerated microscopically using a hemocytometer. The percentage of viable cells recovered after various periods of storage following desiccation compared to the number of viable cells recovered immediately after desiccation was measured by standard Trypan Blue staining and cell counting using a hemocytometer. The results are shown in Table 2 below.

TABLE 2

| Sampling and Assay Time | Percent Viable Condition #1 | Percent Viable Condition #2 |
|---|---|---|
| After Dessication (AD) | 100 | 100 |
| 1 Day AD | 98 | 93 |
| 2 Days AD | 98 | 86 |
| 3 Days AD | 73 | 73 |
| 4 Days PD | 65 | 65 |
| 7 Days PD | 44 | 37 |
| 10 Days PD | 9 | 15 |

EXAMPLE 8

P19 cells, a mouse neural stem cell line, were grown using standard methods. Cells were harvested by standard typsinization and resuspended to a concentration of $10^7$ per milliliter in αMEM media supplemented with 7.5% donor calf serum and 2.5% fetal bovine serum. Twenty microliters of the above cell suspension was deposited on an agarose bed in a cap. The deposited cells were promptly desiccated and stored as described in Example 7. Following a number days the sealed tube/cap assemblies were opened and the cells were recovered by resuspension in 200 microliters of αMEM as described in example 7. The fluid growth media containing most of the cells was removed to a separate tube and cells were examined microscopically using phase contrast optics. In addition, cells were stained with Trypan Blue and live cells were enumerated microscopically using a hemocytometer. The percentage of viable cells recovered after various periods of storage following desiccation compared to the number of viable cells recovered immediately after desiccation was measured by standard Trypan Blue staining and cell counting using a hemocytometer. The results are shown in Table 3 below.

TABLE 3

| Time of Sampling and Assay | Percentage of Viable Cells |
|---|---|
| After Desiccation (AD) | 100 |
| 1 Day AD | 80 |
| 3 Days AD | 54 |
| 6 Days AD | 51 |
| 9 Days AD | 29 |
| 11 Days AD | 7 |

CONCLUSIONS

The above-described examples demonstrate that the above-described methods allow one to preserve tissue culture cells at room temperature or at 37 degrees Celsius for several weeks or longer. Following rehydration and a short period of recovery the cells are restored to healthy, normal growth.

The present invention provides a method to preserve cells by using a readily obtained inexpensive reagent (agarose) and simple easily constructed equipment. Neither low temperature, nor reduced air pressure is required as, for instance with lyophilization. While it is anticipated that desiccation at room temperature and storage at room temperature or higher is the most convenient way to practice the invention it is recognized that desiccation and/or storage of cells at lower temperatures is also likely to result in the preservation of cells that have been induced to aggregate as spheroids and subsequently desiccated as well as cells that are desiccated as non-aggregated cells by the methods described herein. The present invention also provides a composition of matter comprising cells that are desiccated and retain the potential to be recovered as healthy growing cells following addition of fluid media. This method requires little special skill or handling and, while best carried out using a drying chamber as described, other chambers that would result in drying of the cells could be used. Cells preserved by the methods described herein may be stored at ambient room temperature (approximately 20 degrees Celsius) temperatures, or up to 37 degrees, and atmospheric pressure and require no special handling.

REFERENCES

Bloom, F., P. Price, G. Lao, J. L. Xia, J. H. Crowe, J. R. Battista, R. F. Helm, S. Slaughter, and M. Potts. (2001). Engineering mammalian cells for solid-state sensor applications. Biosensors and Bioelectronics. 16: 603–608.

Chun, M. H. (2000) Serum signaling factors and spheroids. Critical Reviews in Oncology Hematology. 36: 89–98.

Guo, N., Puhlev, I., Brown, D. R., Mansbridge, J. and Levine F. (2000). Trehalose expression confers desiccation tolerance on human cells. Nature Biotech. 18: 168–171

We claim:

1. A method for the preservation, for a number of weeks, of cells from immortalized mammalian cell culture lines comprising the steps of:
   a) incubating the cells under conditions which induce formation of spheroids,
   b) removing fluid media from said spheroids,
   c) desiccating said spheroids at a relative humidity of approximately 20% for 12 to 18 hours, and
   d) storing said spheroids in a container that prevents further drying of said spheroids, thereby preserving the cells.

2. The method according to claim 1 wherein said spheroids are stored at about 20 degrees Celsius.

3. The method according to claim 1 wherein said spheroids are stored at about 37 degrees Celsius.

4. The method according to claim 1 wherein said spheroids are stored at a temperature between about 20 degrees Celsius and about 37 degrees Celsius.

5. The method according to claim 1 wherein said cells are induced to form spheroids by incubating said cells on a non-adherent surface.

6. The method according to claim 1 wherein said cells are induced to form spheroids by incubating said cells on a surface of gelled agarose.

7. The method of claim 1, further comprising the step of adding fluid growth media to the spheroids.

8. The method of claim 1, wherein said container is a tissue culture incubator.

9. The method of claim 1, further comprising storing said spheroids under $N_2$.

* * * * *